United States Patent [19]

Bodden

[11] Patent Number: 5,069,662
[45] Date of Patent: Dec. 3, 1991

[54] CANCER TREATMENT

[75] Inventor: William L. Bodden, Branford, Conn.

[73] Assignee: Delcath Systems, Inc., New York, N.Y.

[21] Appl. No.: 260,623

[22] Filed: Oct. 21, 1988

[51] Int. Cl.$^5$ .............................................. A61M 1/00
[52] U.S. Cl. ........................................ 604/4; 604/5; 604/101
[58] Field of Search .................. 604/4, 5, 6, 7, 8, 101; 210/23

[56] References Cited

U.S. PATENT DOCUMENTS

| Re. 28,742 | 3/1976 | Rafferty et al. | 415/90 |
|---|---|---|---|
| 4,867,74 | 9/1989 | Calderon . | |
| 3,647,324 | 3/1972 | Rafferty et al. | 417/420 |
| 3,864,055 | 2/1975 | Kletschka et al. | 415/1 |
| 3,957,389 | 5/1976 | Rafferty et al. | 415/1 |
| 3,970,408 | 7/1976 | Rafferty et al. | 415/60 |
| 4,037,984 | 7/1977 | Rafferty et al. | 415/60 |
| 4,048,064 | 9/1977 | Clark, III | 210/23 |
| 4,192,302 | 3/1980 | Boddie | 604/4 |
| 4,445,892 | 5/1984 | Hussein et al. | 604/101 |
| 4,546,759 | 10/1985 | Solar | 128/1 |
| 4,573,966 | 3/1986 | Weikl et al. | 604/53 |
| 4,610,662 | 9/1986 | Weikl et al. | 604/53 |
| 4,696,668 | 9/1987 | Wilcox | 604/101 |
| 4,714,460 | 12/1987 | Calderon . | |
| 4,820,261 | 4/1989 | Schmoll | 604/4 |
| 4,883,459 | 11/1989 | Calderon . | |

FOREIGN PATENT DOCUMENTS 2834956  2/1980  Fed. Rep. of Germany .
511951  6/1976  U.S.S.R. .

OTHER PUBLICATIONS

V. Wizemann et al., Portocaval Hemofiltrazion During the Anheptic Phase . . . , pp. 485–487.
Pierre M. Galletti et al, Hemodiolysis in Cancer Chemotherapy, pp. 20–24.
Michael W. Horton et al, Continuous Arteriovenous Hemofiltration: . . . , pp. 1361–1367.
Sadao Kamidono et al, A Fundamental Study of Regional Chemotherapy . . . , pp. 176–178.
Winchester et al, Dialysis and Hemoperfusion of Poisons and Drugs, pp. 787–791.
Yukihiko et al, Therapeutic Apheresis: A Critical Look, pp. 93–175; 202–241.
Robert K. Ausman, Development of a Technic for Isolated Perfusion of the Liver, pp. 3993–3997 dated Dec. 1, 1961.

*Primary Examiner*—Robert A. Hafer
*Assistant Examiner*—Kerry Owens
*Attorney, Agent, or Firm*—Elliot M. Olstein; John N. Bain

[57] ABSTRACT

Perfusing a high concentration of an agent to treat an organ, such as anti-cancer agents through a body organ containing a tumor, without their entering the body's general circulation, removing them from the organ with effluent blood and transporting the contaminated blood to an extracorporeal circuit where the blood is treated to remove the contamination, and returning the treated blood to the body. The process prevents toxic levels of the agents from entering the body's general circulation while delivering lethal doses of the agents to the tumor. There are described various apparatus for effecting the intra- and extracorporeal treatment of such contaminated blood.

5 Claims, 3 Drawing Sheets

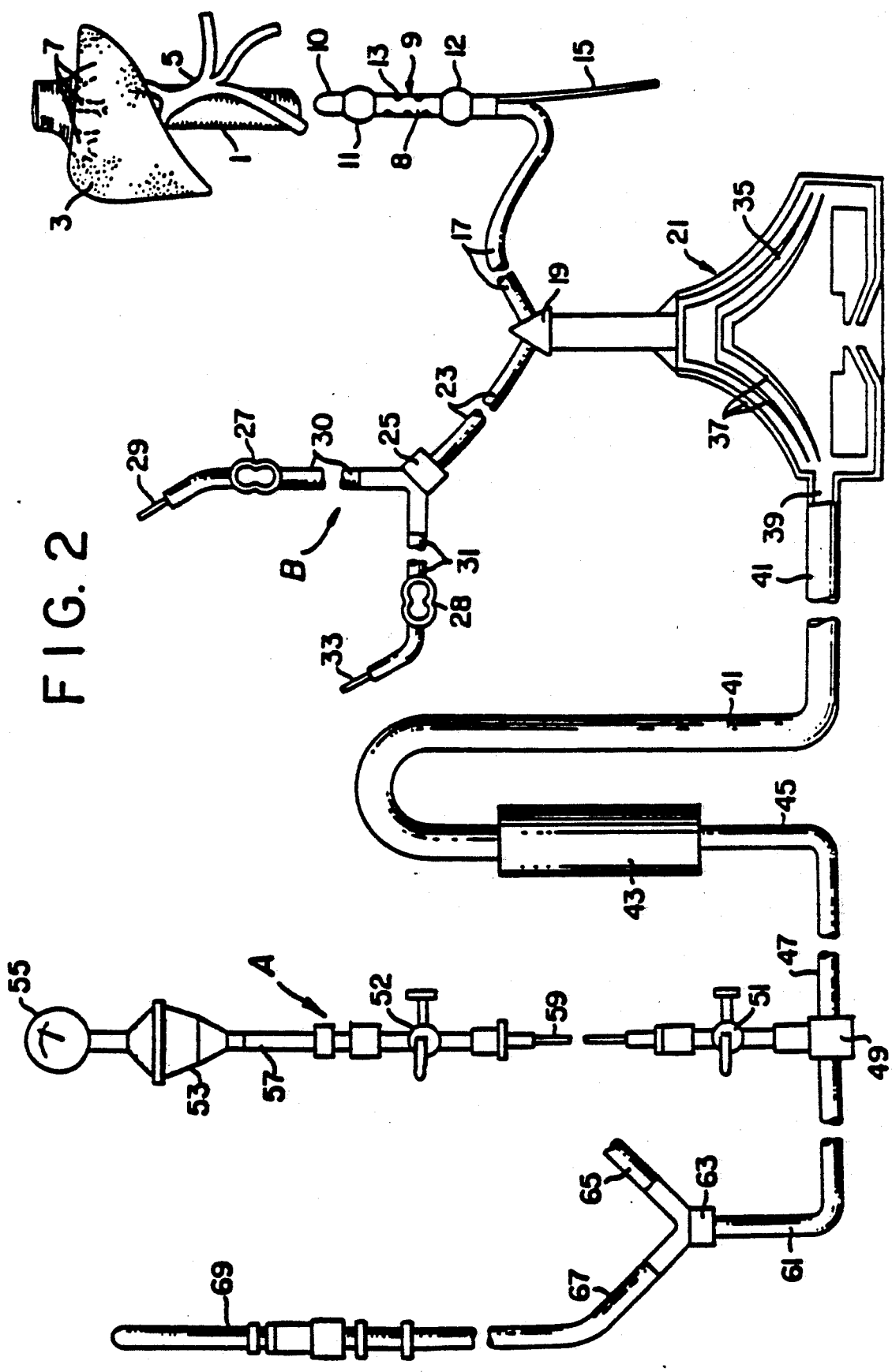

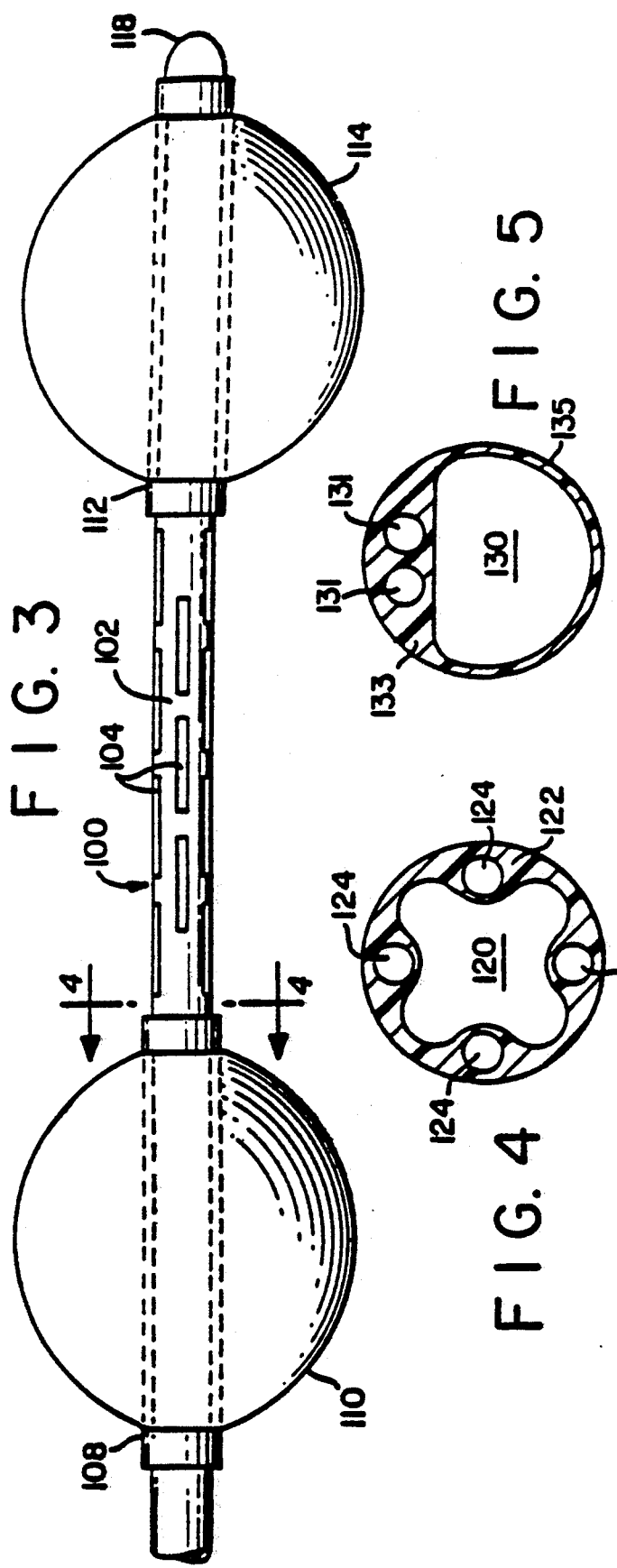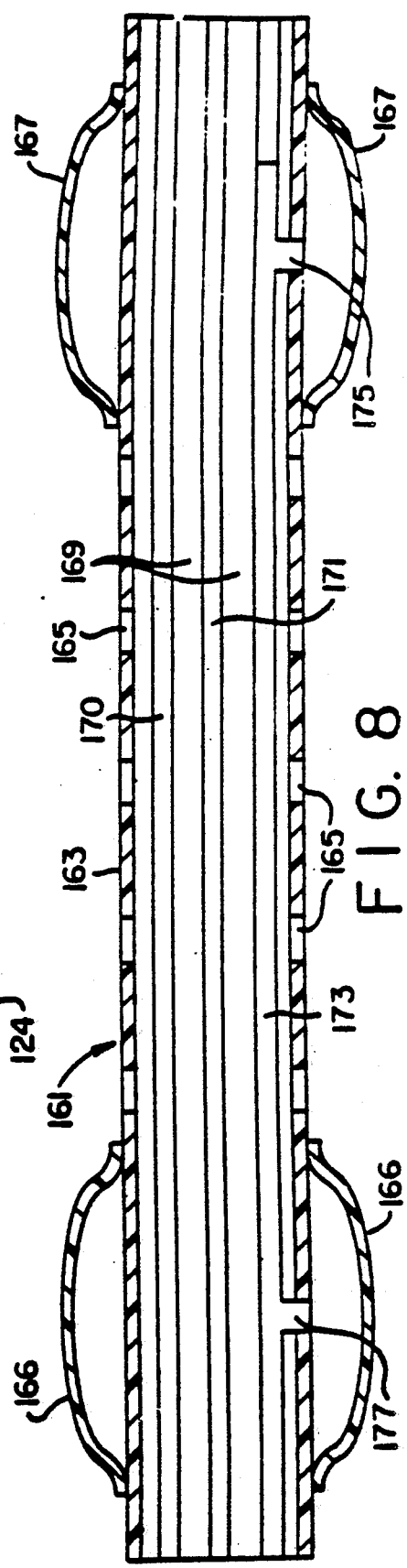

CANCER TREATMENT

BRIEF DESCRIPTION OF THE INVENTION

The process of perfusing a high concentration of anti-cancer agents through a body organ containing a tumor without contaminating the body's general circulation, removing them from the organ with effluent blood, tranporting the contaminated blood to an extracorporeal circuit, treating the blood in the extracorporeal circuit to remove the contamination, and returning the treated blood to the body. The process prevents toxic levels of the agents from entering the body's general circulation while delivering lethal doses of them to the tumor. A variety of apparatus for effecting the intra- and extra-corporeal treatment of such contaminated blood are described.

BACKGROUND TO THE INVENTION

Primary cancer of the liver (hepatocellular tumor, hepatoma) is a disease with a dismal prognosis due to its relentless progression despite many therapeutic modalities. Although uncommon in the United States (approximately 14,000 new cases per year), hepatoma is the most prevalent tumor in the most populous countries of the world. It is quite common in sub-Sahara Africa, Southeast Asia, Japan, the Pacific Islands, Greece and Italy. For those patients not surgically resectable, median survival is approximately 8 weeks. In North America, this malignancy most commonly arises in elderly patients with alcoholic or postnecrotic cirrhosis. However, in other parts of the world, it is epidemic and often occurs in young patients. This demographic variation is correlated with a high incidence of early childhood infection with hepatitis B virus in the geographic areas where hepatocellular tumor is most common.

Although the incidence of primary liver cancer is not high in the United States, cancer of the colon is a major health problem, and cancer of the colon reaches the liver in about 50% of the patients. Over 140,000 new cases are diagnosed yearly. Once the disease has spread, therapy is ineffective, with approximately 50% of all patients dying from their disease within five years of diagnosis. In 15% to 20% of the patients, the tumor will have spread to the liver by the time of diagnosis, and in over 50% of patients, colon cancer will eventually spread to the liver metastasis even when there is no tumor spread elsewhere. Tumor cells reach the liver via the portal vein and establish a blood supply from the hepatic artery, perhaps through the elaboration of tumor angiogenesis factor(s).

The impact of colon cancer on the liver is grim. When liver metastases are diagnosed, the median survival time falls to 4-9 months without treatment. While tumors that originate in other organs do not spread to the liver as frequently, their prognosis is also significantly worsened when they reach the liver. Much medical research assumes that effective treatment of tumors in the liver will extend survival, improve quality of life, and reduce the financial and emotional impact of this disease.

It is a widely held view, and currently being acted upon, as noted below, that effectiveness of chemotherapy is improved by intraarterial infusion. However, systemic toxicity has limited drug tolerance. Detoxification of blood containing chemotherapeutic agents has not been developed until this invention.

The current treatment modalities for colon tumor metastatic to the liver are unsatisfactory. A solitary metastatic deposit of colon cancer is best handled by surgical resection, which leads to a 1 year survival rate of 80% and a 3-year survival rate of 40%. However, in 95% of the cases, multiple metastatic lesions are present. Systemic chemotherapy has little lasting effect on these metastatic lesions. Although certain drugs have shown activity in various studies, when used at higher doses their effects are negated by their systemic toxicities. These same drugs may prove to be much more effective if their systemic toxicities can be avoided. A treatment which exposes a tumor to high antineoplastic drug concentrations and removes the drug from the blood before systemic exposure occurs may be an effective therapy for cancer in the liver.

At present surgical resection offers the only chance of cure of hepatoma. For resection to be possible, at least one hepatic segment must be spared. The uninvolved segment(s) of liver must be free of cirrhosis. Unfortunately, the proportion of patients with potentially resectable tumors is small.

Hepatic artery infusion (HAI) of chemotherapy has been widely investigated. Arterial infusion of 5-FU and FUDR increases their effectiveness by delivering the drug directly to liver tumor cells before its dilution by the systemic circulation. This approach is attractive because hepatocellular tumors frequently remains localized to the liver, and, like most chemotherapeutic drugs, 5-FU displays a dose-response effect, i.e., increasing the dose can give a proportionately greater increase in effect. Also, certain drugs, including the fluorinated pyrimidines, doxorubicin and others, are metabolized by the liver and excreted through the biliary tract thereby reducing systemic drug toxicity.

Initially, chemotherapy was given via percutaneously placed catheters with the use of external pumps. Response rates obtained with this form of treatment in patients with colon cancer metastatic to the liver was generally superior than those attained when identical drugs were given intravenously, with objective responses seen in 34% to 83% of the patients. More recent studies, employing surgically placed catheters and implanted pumps, have yielded response rates in 50% to 60% (range 20% to 88%) of the patients with colon cancer metastatic to the liver. The fluorinated pyrimidines (5-FU and FUDR) are the drugs most commonly used for prolonged (over 1 to 2 weeks) HAI, while Mitomycin C and other drugs have been given alone or in combination with these drugs as intermittent bolus injections into the hepatic artery. To date, no randomized comparative studies have demonstrated that HAI administration of fluorinated pyrimidines is therapeutically superior to systemically administered drug. Local and systemic toxicities limit the amount of therapy which can be delivered even by the arterial route.

Local toxicities [1] in the gastrointestinal tract have included gastric and duodenal ulceration, gastric bleeding and/or perforation, severe dyspepsia, gastritis and diarrhea. Many of the patients who developed these local toxicities were found to have had a misplaced or dislodged catheter tip. In these cases, the drug was perfusing a large portion of the stomach and duodenum via the gastric arteries. Gastrointestinal toxicities did not occur when the gastric arteries were separated and ligated from the hepatic artery or embolized at the time of catheter placement. Diarrhea, a systemic toxicity of the fluorinated pyrimidines, occurs more commonly in patients with arterial to venous (A-V) shunting of 30% or greater. A-V shunting allows drug to bypass functioning liver cells and avoid being metabolized by the liver thereby increasing systemic drug exposure.

1. Toxicity resulting from unintentional injection of drug into an artery other than a hepatic artery, most often gastric or duodenal branches.

Local hepatobiliary toxicities (hepatitis, cholecystitis, biliary sclerosis, stenosis and stricture) occur in up to 50% of the patients treated with conventional HAI 5-FU or FUDR chemotherapy. The gallbladder and biliary tree receive all of their blood supply from the hepatic artery whereas the liver receives approximately one-fourth of its blood supply from the hepatic artery. Biliary tract toxicity seems to be more common in patients who have had the blood supply to the biliary tree disrupted by ligation of the gastric arteries. Choliangiography, CT scanning and alkaline phosphatase elevations have been shown to be effective monitoring tools for identifying patients with impending biliary tract toxicity. Hepatitis, manifested by nausea, vomiting, abdominal pain and jaundice in association with elevated serum concentrations of liver transaminases and bilirubin has occurred in patients receiving conventional HAI 5-FU or FUDR. Hepatitis appears to be related to the dose and duration of the hepatic arterial drug infusion.

Systemic toxicity of HAI chemotherapy has not been a major problem when drugs with a high liver extraction ratio, such as 5-FU and FUDR, have been given in conventional doses that are defined by systemic toxicity. Drugs which are not substantially metabolized by the liver upon first pass often cause system toxicities, primarily myelosuppression, when given intraarterially. Obviously, without the use of a detoxifying system that removes unmetabolized drug, most drugs cannot be employed in higher, potentially more effective, doses by the HAI route.

Systemic chemotherapy for hepatocellular tumor remains a therapeutic challenge. Numerous agents have been tested in Phase II trials; objective responses to therapy are uncommon. 5-FU and doxorubicin (Adriamycin) are the only drugs which have consistently been shown to have significant activity. Initial reports of East African blacks treated with doxorubicin, 75 mg/m$^2$ every 3 weeks, resulted in 22 patients attaining an objective response (3 complete) in 50 patients treated. Substantial toxicity occurred with the use of doxorubicin at this dose. Hence, most other studies report on the use of doxorubicin, 60 mg/m$^2$ every 3 weeks. At this dose, objective therapeutic responses occurred in approximately 20% of the patients.

Ausman, R. K. (1961) *Development of a technic for isolated perfusion of the liver*, N.Y. State J. Med., vol. 61, p. 3993. discloses isolating the liver by surgically separating the portion of the inferior vena cava which includes the hepatic veins, infusing a chemotherapy agent to the liver through the splenic and common hepatic arteries, and collecting the chemotherapy agent from the isolated portion of the inferior vena cava. This reference does not disclose a method for detoxifying blood of chemotherapeutic agent.

K. Schwemmle and K. Aigner, *Recent Results in Cancer Research*, vol. 100, pp. 229-233, pub. by Springer-Verlag, Berlin, 1986, utilized isolated hepatic perfusion in two patients suffering from disseminated hepatic metastases of colorectal cancer. They characterize their work, and that carried out prior to their efforts, as follows:

"Among the various treatment modalities for liver metastases such as resection, intraarterial infusion, isolated perfusion, or chemoembolization, isolated perfusion enables chemotherapeutic agents to be added to the perfusion circuit in dosages higher than could be tolerated by systemic administration. The upper limit of dosage is only the local toxicity. Because hepatic metastases are mainly vascularized by the hepatic artery, intraarterial infusion of anti-cancer agents provides a much higher concentration of the drug in these tumors than can be achieved by systemic chemotherapy.

"To develop a method for intraarterial treatment with maximal doses of chemotherapeutic drugs, we started with isolated perfusion of the liver in animal experiments according to previously published methods [4-6]. Optimal surgical techniques and drug toxicity were studied in dogs. After these studies in animals had proved that the method was practicable and safe, in November 1981 we performed an isolated hepatic perfusion in two patients suffering from disseminated hepatic metastases of colorectal cancer [1]. After these two patients had survived 5 months without complication, another 38 patients were submitted to isolated hyperthermic perfusion of the liver with chemotherapeutics [2].

"In the isolated perfusion circuit both the hepatic artery and portal vein are perfused and the hepatic venous return is collected via a single venous line. During isolated perfusion a portocaval shunt is established in which ammonium is filtered out of the portal blood (FIG. 1). Recently, we have omitted the filtration unit.

"During the operative procedure through an abdominal midline incision the liver, the hepatoduodenal ligament, and the inferior caval vein are exposed. Tourniquets are placed around the gastroduodenal artery and portal vein and around the caval vein below and above the renal veins as well as intrapericardially.

"In order to collect the hepatic venous outflow a double-channel catheter is inserted into the caval vein from below the renal veins. This special catheter consists of a longer channel shunting the caval vein to maintain cardiac venous return and a second shorter channel for the isolated hepatic venous return. The portocaval shunt tube is inserted into the caval vein channel, whereas two lateral openings collect the venous return from the kidneys.

"After the perfusion catheter is inserted into the caval vein the portal vein is cannulated in both directions. The peripheral catheter is connected to the portocaval filtration unit consisting of a roller pump and a hemofiltrating system. At flow rates of approximately 300-400 ml portal venous blood has been filtered and with adequate volume substitution returned to the caval shunt tube. Thus blood levels of ammonium have been kept within normal ranges during the period of isolated hepatic perfusion. In case of leakage to the systemic circulation a part of the anti-cancer drugs as well has been filtered out in that portacaval shunt. As soon as the shunt is established, the common hepatic artery is clamped and perfusion is started via the central portal vein catheter in a partial circuit. Then the arterial catheter is inserted into the gastroduodenal artery and the liver is perfused via two arterial lines at a flow rate of 200-350 ml/min in the hepatic artery and 150 ml/min in the portal vein. Heating the perfusion circuit the temperature of the hepatic tissue is increased. The temperature, which should not exceed 40° C., is measured with needle probes in the right and left liver lobes. In our first 31 isolated liver perfusions we only applied 5-fluorouracil (5-FU) in a dosage between 500 and 1000 mg. In the last eight patients a combination consisting of mitomycin C and 5-FU was used.

"Few complications occurred after isolated liver perfusion. Three patients died a short time after the operation. One patient died 2 hours later from untreatable bleeding after an isolated hepatic perfusion combined with a hemihepatectomy. The tumor had already infiltrated the caval vein. In another patient septicemia and respiratory distress occurred 6 days after the perfusion. The third patient died from renal failure 2 weeks after the perfusion. His autopsy showed a 90% regression of the tumor. Seventy percent of the hepatic tissue in this case had been involved in metastases. In the last 30 patients there were no fatal outcomes.

"In spite of the increased survival time unfortunately in the combined group the patients developed extrahepatic metastases after the treatment. In ten cases (83%) metastases of the lung developed. Half of the patients developed peritoneal carcinosis or at least positive lymph nodes at the hepatoduodenal ligament and in three cases (25%) recurrences at the colorectal anastomoses or at the perineal scar developed."

"In conclusion we see the following advantages of liver perfusion:
1. We are able to use a high anti-cancer dosage which cannot be achieved by other methods, for example, intermittent or continuous intraarterial infusion.
2. The administration of the anti-cancer agents is performed via both the hepatic artery and the portal vein.
3. A combination with hyperthermia is given.

"*The most important disadvantage of this method is the fact that the perfusion cannot be repeated. However, it is possible at any time to continue the therapy with intraarterial infusions and/or with chemoembolization.*" (Emphasis supplied)

The following publications relate generally to perfusing individual organs with chemotherapy agents: Creech et al.[2], Healy[3], Healy, et al.[4], Pierpont, et al.[5], and Shingleton, et al.[6] None discloses detoxifying blood which has passed through an isolated organ and returning the detoxified blood to the patient.

[2]. *Annals of Surgery*, vol. 148, no. 4, pp. 616–632 (October 1958), note summary at page 632: "Chemotherapy of cancer has not been entirely satisfactory because the administration of doses large enough to significantly affect a tumor produce serious toxic effects on the bone marrow and gastrointestinal tract."
[3]. *Surgery-Gynecology Obstetrics*, vol. 120, no. 6, pp. 1187–1193 (June, 1965)
[4]. *JSR*, vol. I, no. 2, pp. 111–116 (July, 1961) (deals specifically with liver isolation)
[5]. *J. Thoracic and Cardiovas. Surg.*, vol. 39, no. 2. pp. 159–165 (February, 1960)
[6]. *Annals of Surgery*, vol. 152, no. 4, pp. 583–593 (October, 1960)

The following publications disclose applying a chemotherapy agent to a specific organ, collecting blood generally from the patient, detoxifying the blood, and returning the blood to the patient: Kamidono, et al.,[7] and Agishi.[8]

[7]. *The Journal of Urology*, vol. 131, pp. 36–40 (1984) and *Investigative Urology*, vol. 19, No. 3, pp. 176–178
[8]. Said to have utilized "selective delivery of the anticancer drug is achieved by percutaneous injection of 1 mg/kg of mitomycin C into a drug-chamber of an operatively implanted vascular access port another end of which is inserted in the feeding artery of the cancer-bearing organ."
"Removal of the drug is performed by the usual method of charcoal hemoperfusion," Dr. Agishi stated. "However, in order to augment the anticancer effect, local hyperthermia is established utilizing a radiofrequency wave—13.56 MHz—emission apparatus." (Miles Pharmaceutical Oncology News Update, 1987)

Krementz, *Cancer*, vol. 57, no. 3, pp. 416–432 (1986), reviewed the development of regional chemotherapy by perfusion. He stated the following regarding liver perfusion performed surgically in an animal:

"Techniques for perfusion of the liver have been complicated, and represent major abdominal surgery. Our techniques, developed for the experimental animal and applicable to patients, involved isolation of the liver by passing a Foley balloon catheter (Bard Urological Division, Murray Hill, N.J.) with a ligated tip through the vena cava from the femoral vein to a point proximal to the hepatic veins. The vena cava was occluded above by the balloon that was positioned above the diaphragm and below the hepatic veins by a snare placed above the renal veins (FIG. 7), and the hepatic vein drainage was returned to the pump reservoir through the catheter. The hepatic artery was temporarily clamped, and oxygenated blood, and oxygenated blood from the pump and the chemotherapeutic agents were delivered to the liver through the proximal portal vein. Blood from the distal portal vein and vena cava was returned to the heart through an accessory bypass from the femoral vein to the external jugular vein. We did not persist in our efforts to use hepatic perfusion clinically, but other investigators have separately developed techniques for perfusion of human livers. The approach developed by Aigner and colleagues uses a double-lumen tube to collect hepatic venous blood in the outer tube, with bypass of the distal caval blood through the inner tube. Arterial blood and chemotherapy are delivered through the hepatic artery and proximal protal [sic: portal] vein to the liver. This method is under study, particularly in Germany, and has been performed safely with acceptable morbidity."

Double balloon catheters in general are described in the following references:

Weikl, et al., U.S. Pat. No. 4,573,966, patented Mar. 4, 1986, and U.S. Pat. No. 4,610,662, patented Sept. 9, 1986, describe the use of double balloon catheters to treat stenosis;

Solar, U.S. Pat. No. 4,546,759, patented Oct. 15, 1985, is directed to a triple balloon catheter to assist right ventricle functioning;

Hussein, et al., U.S. Pat. No. 4,445,892, patented May 1, 1984, relate to a dual balloon catheter for insertion in blood vessels to provide an isolated operating region in the vessel between the balloons which facilitates the use of an optic system;

Baran, et al., U.S. Pat. No. 4,423,725, patented Jan. 3, 1984, describe a multiple surgical cuff alleged to have a variety of uses.

Betancourt, U.S. Pat. No. 4,180,076, Dec. 25, 1979, describes a nasogastric catheter containing two inflatable vessels.

German Offenlegungsschrift 28 34 956 and Russian Patents 651817 and 511951 describe the use of double balloon catheters for use in isolating the liver for the purpose of blocking blood flow from the liver. The catheters are provided with a bypass to allow blood flow to continue through the artery. Russian patent 511951 describes the use of a perforated wall catheter for removing blood from the liver and isolating it via a pump, and with respect to the perfusion of the liver with medicants and coolants, the perfusate is collected and returned to the liver via a pump.

Implantable pumps have recently come into vogue. However, studies have indicated that a large proportion of the patients developed toxicity due to the systemic effects of chemotherapy.

In summary, chemotherapy has not made a dramatic impact on the treatment of primary or metastatic liver cancer. Certain drugs and biologicals have shown considerable activity in various studies, but their effects are negated by systemic toxicity. Some of these may prove to be much more effective if their systemic toxicity can be eliminated.

A treatment which exposes tumors to high concentrations of antineoplastic drugs and biologicals and removes them from the blood before systemic exposure would be an advance in therapy for cancer in the liver. Moreover, it would be desirable to have a method which allows the opportunity for exploring HAI therapy with a variety of drugs and biologicals at dosage levels higher than ever before found tolerable by the body A process which allows the variations in the kind and dosage of chemotherapuetic agents to livers would be a significant advance in the treatment of such cancers. A process that does not require general anesthesia or surgery, and is sufficiently non-invasive to allow frequent repetition of therapy would be a significant advance in the art. There is described herein a process which provides such advantages.

THE INVENTION

This invention relates to a process of perfusing a high concentration of anti-cancer agents through a body organ containing a tumor without contaminating the body's general circulation, removing them from the organ with effluent blood, transporting the contaminated blood to an extracorporeal circuit, treating the blood in the extracorporeal circuit to remove the contamination, and returning the treated blood to the body. The process prevents toxic levels of the agents from entering the body's general circulation while delivering lethal doses of them to the tumor. A variety of apparatus for effecting the intra- and extracorporeal treatment of such contaminated blood are described.

The process of the invention embraces a system of non-operative and sufficiently non-invasive intracorporeal and extracorporeal means to allow frequent repetition of therapy, if desired, which comprises perfusing at an anti-cancer agent to a tumor, collecting and containing the contaminated blood emanating from the tumor without general circulation of the contaminated blood to the body, transporting the contaminated blood from the body to an extracorporeal treatment system, removing anti-cancer agent from the blood in the extracorporeal treatment system, and returning the treated blood to the body.

There is described a technique by which anti-cancer agents, such as chemotherapeutic agents, can be removed from the hepatic venous blood before entering the systemic circulation. This permits safe infusion of greater than usual concentrations of anti-cancer agents, such as cytotoxic levels of chemotherapeutic agents, into the hepatic artery for treatment of tumors of the liver. However, the invention in its broadest sense, allows the treatment of a variety of tumor-bearing organs with anti-cancer agents, such as chemotherapeutic agents, while avoiding systemic toxicity.

The invention encompasses a process of treating organ site tumors which comprises a. exposing a tumor in a body organ to one or more anti-cancer agents in higher than usual concentrations, b. removing from the organ effluent blood contaminated with the agent provided to the organ, without systemic exposure to the body, c. passing the effluent blood from tributary veins in the organ into a larger vein in which has been provided a catheter containing i. at least one inflatable balloon provided to obstruct passage of the effluent blood to the heart and ii. an avenue, such a plurality of openings or a large opening, in the catheter sufficient to accommodate the volume of effluent blood traversing the tributary veins, d. transporting the contaminated effluent blood through the catheter and thence from the body into an extracorporeal circuit, e. detoxifying the blood in the extracorporeal circuit, and f. returning the detoxified blood to the body.

More particularly, the invention relates to the treatment of organ site tumors which comprises a. exposing a tumor in a body organ to one or more anti-cancer agents such as antineoplastic drug and biological response modifiers in higher than usual concentrations, b. removing from the organ effluent blood contaminated with the agent provided to the organ, without systemic exposure to the body, c. passing the effluent blood from tributary veins in the organ into a larger vein in which has been provided a catheter containing i. spaced-apart inflatable balloons provided to obstruct the large vein above and below said tributary veins and ii. an avenue, such a plurality of openings or a large opening, in the catheter between the balloons sufficient to accommodate the volume of effluent blood traversing the tributary veins, d. transporting the contaminated effluent blood through the catheter and thence from the body into an extracorporeal circuit, e. detoxifying the blood in the extracorporeal circuit, and f. returning the detoxified blood to the body.

In respect to the defined treatment, the extracorporeal circuit or treatment system comprises (a) means for transporting the contaminated blood to (b) means for separating the drug concentration from the blood and also returning the decontaminated blood to the body.

The invention has particular importance in the antineoplastic treatment of tumors of the liver since anticancer levels of antineoplastic agents can be safely infused into the hepatic artery for treatment and systemic toxicity can be avoided. The invention involves intraarterial infusion of the liver with antineoplastic agents and removal of the antineoplastic agents from the hepatic venous blood before it enters the systemic circulation. This invention includes the percutaneous insertion of a special double balloon catheter into the inferior vena cava. The catheter contains two inflatable balloons appropriately spaced to obstruct the inferior vena cava above and below the hepatic veins. Hepatic venous blood is drawn through fenestrations in the catheter wall and thence into an extracorporeal circuit that is openly connected with the catheter's lumen. The blood is decontaminated in this circuit and then returned to the systemic circulation via either a subclavian vein, an external jugular veins, the superior vena cava or the right atrium.

The invention includes the use of detoxification means, such as one or more of: a hemoperfusion cartridge, hemodialysis, hemofiltration, and hemoadsorbtion through antibodies or biological ligands or molecules able to render them nontoxic and/or to clear the blood of the antineoplastic agent and allow the re-administration of the patient's own detoxified blood. The invention embraces the passage of the contaminated blood from the double balloon catheter through tubing into a pump that assists the passage of the contaminated blood to a detoxification means such as a hemoperfusion cartridge containing one of a variety of substances, such as a sorbing solid, and/or a hemodialysis unit that removes the drug from the blood. The treated blood is returned to the body via an appropriate large caliber vein.

The invention also includes a disposable kit, that may be used, e.g., for inpatient hospital use with cancer patients, comprising a double balloon catheter, a detoxification means, piping and valves. The kit may include for guidewires, heparin, and other related equipment.

The invention encompasses a double balloon catheter capable of
a. being percutaneously inserted into the inferior vena cava,
b. closing off the flow of contaminated blood from the hepatic veins, and
c. recovering the contaminated blood from the hepatic veins.

A variety of novel catheters are described that may be used for the recovery of contaminated blood derived from an organ containing a tumor that has been perfused with a anti-cancer agent for its treatment, and for the removal of the contaminated blood from the body so that the blood can be detoxified outside of the body.

BRIEF DESCRIPTION OF THE DRAWING

FIG. 2 shows a diagrammatic and semi-schematic view of an apparatus assembly for carrying out the process of the invention.

FIG. 3 shows a partial cross-sectional side view of one design of a double balloon catheter useful in the process of the invention.

FIG. 4 shows a cross-sectional end view of the shaft of the double balloon catheter of FIG. 3.

FIG. 5 shows a cross-sectional end view of the mid-section of a modification of the double balloon catheter of FIG. 3.

FIG. 8 shows a cutaway cross-sectional side view of the interior of a double balloon catheter encompassed by the invention.

DETAILS OF THE INVENTION

Figure 1:
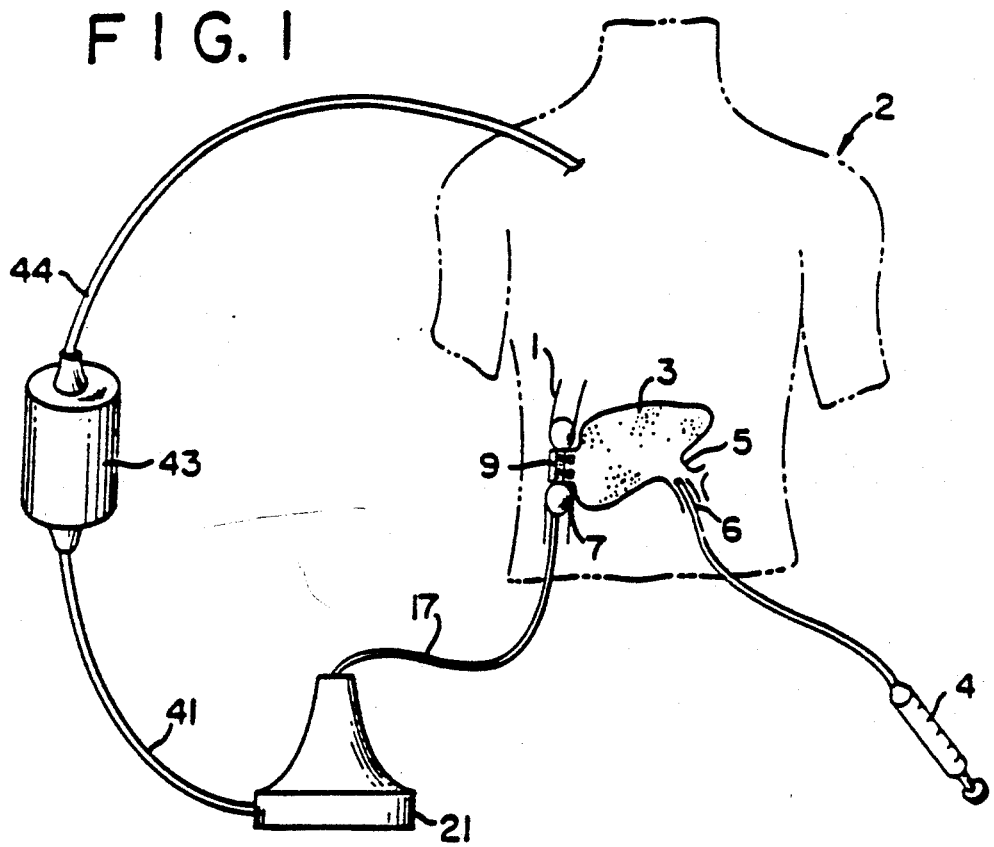
FIG. 1 shows a diagrammatic and schematic view of significant apparatus features in relationship to the body for carrying out the process of the invention.

The process of the invention avoids the use of surgery to isolate the flow of contaminated blood and returns the same blood but in a more purified condition to the patient. As a result, the process of the invention may be used for extended periods of time, indeed, for periods of time far longer than previously used in the treatment of the same tumors.

The process of the invention is applicable to the treatment of a number of tumors such as those of the kidney, liver, pancreas, bladder and pelvis. Primary and metastatic liver tumors are especially treatable by the process of this invention. As pointed out above, many of them have shown responsiveness to chemotherapeutic drugs.

In the most preferred case, the invention is directed to the treatment of tumors in the liver by the use of one or more antineoplastic agents, such as chemotherapuetic agents and/or biologicals, and the purification of venous blood from the liver to avoid systemic circulation of the agent(s). This may involve the use of balloon catheters that are suitable for insertion in the inferior vena cava to isolate venous outflow from the liver and permit the removal of blood contaminated with antineoplastic agent from the body with a pump. The contaminated blood will be filtered through detoxifying means and then returned to the patient via a large caliber systemic vein at a point above the diaphragm. Because primary hepatocellular and metastatic hepatic tumors derive their blood supply from the hepatic artery, the tumor will be perfused by high concentrations of, for example, a chemotherapeutic agent such as 5-FU or biologicals. Because a normal liver receives three-fourths of its blood supply from the portal vein the drug or biological will be diluted by a factor of about three before it reaches normal, uninvolved liver cells, thereby protecting them against hepatotoxicity.

As noted above, significant elements of this process have been tested in man. In a manner, each component of the system (HAI arterial catheter infusion of chemotherapy, hemodynamic isolation of the hepatic veins by balloon catheters, hemofiltration of 5-FU, and subclavian vein insertion) has been used in humans. However, an extracorporeal drug removal approach with hepatic isolation has only been performed by laparotomy.

THE CATHETERS

As mentioned above, the process of the invention involves the percutaneous placement of unique double balloon catheter designs. These catheters may use a variety of designs and sizes depending on the organ whose veins are isolated and the sizes and locations of its veins. The primary function of the double balloon catheter is to isolate the flow of blood from the veins carrying the effluent blood from the organ containing the tumor that is under treatment. Venous isolation precludes systemic perfusion of the contaminated blood. Thus the tip of the double balloon catheter is to be placed in the body so that the venous effluent from the organ being treated is prevented from flowing to the heart. The space between the two balloons is predetermined to ensure removing the full quantity of contaminated blood from the treated organ. The space between the balloons is large enough that the balloon central in position can be located in a position in the most central draining vein to block contaminated venous blood flow to the heart and the balloon peripheral in position can be located peripheral in the most central draining vein to block the flow of uncontaminated blood to the contaminated venous blood flow. Veins from organs not under treatment can enter the segment between balloons without detrimental effect as long as the pump and filtration system can accommodate the additional volume. The venous anatomy of the organ under treatment or of adjacent organs can be altered where necessary by obstruction using angiographic embolisation or ablation techniques and materials, including detachable balloons or stainless steel coils.

The lumen of the catheter between the balloons is openly connected, or can be made openly connected, to the surrounding vein. In addition, the same lumen of the catheter is also openly connected, or can be made openly connected, to the extracorporeal circuit, thereby providing free flow of the contaminated blood from the veins to the extracorporeal circuit. Thus the catheter has a main lumen to act as a conduit for the contaminated blood flow from the venous effluent(s) to the extracorporeal circuit.

The size of the main lumen is determined by the material of which it is made, the volume of blood to be transported through it and the diameter of the vein in which it will be located. The main lumen may be an open annulus or semi-annulus located within the peripheral balloon that is openly connected to the extracorporeal circuit. In this type of catheter, a central rod or rodlike axis is provided for support for the balloons.

The catheter may also have supplemental lumina. The supplemental lumina are smaller in size, i.e., in diameter or cross-sectional area, than the main lumen. They may serve any of a number of ancillary functions in the process. For example, in one design, a supplemental lumen courses through the full length of the catheter for the purpose of accommodating a guidewire that is desirable for percutaneous insertion of the catheter. Each balloon may be provided with a supplemental lumina to be used for its inflation, or one supplemental lumen may be used for supplying fluid for the inflation of both balloons. An additional supplemental lumen may be provided for connection to a pressure monitor to continuously measure the pressure of the venous effluent. This lumen can also be used to inject contrast medium, if provided with a connector that can accommodate an injection device. In some designs, the main lumen may be used for one or more of the above functions. This multifunctionality can serve to reduce the cost in making the catheter and simplify the apparatus. The main and/or supplemental lumina may be made from separate tubing threaded into the catheter or from channels molded into the structure of the catheter. Another supplemental lumen can be used to return detoxified blood to the general circulation and avoid puncture of another vein.

The wall(s) of the segment of the catheter between the balloons is/are provided with fenestrations to allow entry of venous blood into the main lumen. The number, shape and size of the fenestrations may vary according to the size of the catheter, the rate and volume of blood they must transmit, and the materials of construction of the catheter. The shape and size of the fenestrations should take into consideration turbulence effects as the blood courses though the fenestrations and into the main lumen. Fenestrations that are too small can elevate hepatic sinusoidal pressure and fenestrations that are too large may weaken the catheter walls and compromise the integrity of the catheter.

One practical double balloon catheter design would have one large central lumen, 2 smaller lumina and 2 inflatable balloons that are separated by about 9 to 10 cm. in the length of catheter that contains perforations.

The catheter is designed to be positioned (under fluoroscopic guidance) in the inferior vena cava (IVC) such that the central balloon, when inflated, occludes the IVC just above the hepatic veins. The peripheral balloon, when inflated, occludes the IVC just below the hepatic veins, thus isolating hepatic venous blood from the systemic circulation. Perforations in the catheter between the two inflated balloons convey blood through the large central catheter lumen to a variable speed pump and filtering device. An inferior vena cavagram through the main lumen can be used to document complete obstruction of the inferior vena cava proximal and distal to the hepatic veins. The effectiveness of passage of blood from the liver through the extracorporeal circuit can be monitored by pressure measurement in the central catheter lumen. The variable speed pump is adjusted to maintain normal hepatic vein pressure and flow. The detoxifying means reduce the chemotherapeutic agent such as 5-FU in the blood to nontoxic levels before the blood is returned to the systemic circulation.

In another design an independent return lumen courses through the main lumen. One end to the return lumen is connected to the outlet of the extracorporeal circuit and the other end openly outlets into a vein at a location superior to the diaphragm. When the double balloon catheter is located in the IVC, this return lumen extends beyond the end of the main catheter to the right atrium. In this construction, the return lumen consists of a separate piece of tubing threaded inside the main lumen and through the end hole of the catheter. The return lumen is large enough to carry the full volume of the blood being returned to the patient from the detoxifying apparatus. In another embodiment of the invention, part of the return flow of the effectively detoxified blood is fed through the return lumen and the remainder is separately fed to the patient via a separate feed system, such as through a separate catheter feed to one of the subclavian veins, as described by Krementz, supra.

The double balloon catheter, once properly located in the body, extends through the skin to the outside of the body. It terminates in a Luer fitting and a valve cutoff such as a stopcock. The extracorporeal circuit can be separated from the double balloon catheter and reconnected at will. When the balloons are not inflated, blood flow through the IVC is maintained. When the balloons are inflated, the blood below the peripheral balloon will find secondary pathways to the heart.

This convenience may be duplicated on the supply side of the process, where the chemotherapuetic agent is supplied to the arterial side of the liver, via the hepatic artery, by the percutaneous insertion of a feed catheter to the hepatic artery, leaving the tubular ending of the feed catheter in a plastic reservoir surgically implanted just below the patient's skin and surgically tied therein below the skin. The plastic reservoir contains a resealing membrane of a type similar to those used in multi-dose vials that can be percutaneously penetrated from the outside of the body by one or more needles to reinitiate the flow of chemotherapuetic agent to the diseased organ. Illustrative of such devices is Implantofix ® Drug Delivery System, sold by Burron Medical Inc., 824 Twelfth Avenue, Bethlehem, Pa. 18018.

The double balloon catheter can be introduced into the femoral vein using the Seldinger technique. A guidewire made of stainless steel is first passed through a needle that has been inserted percutaneously into the vein. A catheter with a single balloon is inserted over the guidewire and the balloon is inflated to dilate the percutaneous tract to the diameter of the sheath that will transmit the double balloon catheter. A plastic sheath tubing is passed over the guidewire when the single balloon catheter is removed. After the sheath is properly located in the vein the double balloon catheter is inserted within the sheath and over the guidewire and advanced to the proper position relative to the organ to be treated. All manipulations of the double balloon catheter are done under fluoroscopic control. An inferior vena cavagram can be performed prior to catheter insertion or prior to balloon inflation with the patient lying on an opaque ruler, parallel to the IVC. The hepatic veins and renal veins can be identified and their location determined according to the opaque ruler.

Under fluoroscopic guidance, the catheter is positioned so that the central balloon, when inflated, occludes the IVC just above the hepatic veins. The peripheral balloon, when inflated, occludes the IVC just below the hepatic veins. Dilute contrast medium such as saline solution is used to inflate the balloons and reference to the ruler insures their accurate positioning.

In a specific embodiment of the invention, the double-balloon catheter contains three lumina. One lumen transmits an angiographic guidewire and is used for percutaneous insertion. A main lumen carries hepatic venous blood from the fenestrations between the balloons to the extracorporeal circuit. The third lumen terminates at the fenestrations and is used to measure pressure or inject contrast medium. A pressure monitor, attached to this lumen, measures pressure within the isolated segment of the vena cava before and during balloon inflation. The pressure measured before balloon inflation is the systemic venous pressure. The pressure measured after balloon inflation but before opening the extracorporeal circuit is equal to the wedge hepatic venous pressure, which is assumed to be equal to portal pressure. This measurement can determine the presence or absence of portal hypertension. The pressure measured after balloon inflation and during flow through the extracorporeal circuit is the hepatic venous pressure. The hepatic venous pressure can be monitored continuously during drug infusion. The speed of the pump in the extracorporeal circuit can be adjusted to maintain hepatic venous pressure above systemic venous pressure but below portal pressure. This prevents hepatic sinusoidal congestion. The caliber of the balloon catheter and of the tubing in the extracorporeal circuit are calculated to ensure that they are of sufficient size to transmit the necessary volumes of blood with minimal resistance.

After inflation of the balloons, an inferior vena cavagram (contrast medium injected into the inferior vena cava) is typically performed through the double balloon catheter prior to infusion to document complete obstruction of the vena cava proximal and distal to the hepatic veins and to demonstrate the anatomy of the hepatic veins. Samples of hepatic venous blood are generally aspirated through the pressure port of the double balloon catheter immediately after the beginning of infusion, and, in the typical case, at intervals not to exceed one hour during infusion, and for at least three hours after infusion, the samples are analyzed for chemotherapy agent concentrations. Simultaneous blood samples are taken from the extracorporeal circuit after detoxification and analyzed for drug concentrations in order to document the efficiency of the detoxification means in removing the drug from the blood before returning the blood to the systemic circulation. In addition, blood samples are obtained from a peripheral vein to evaluate drug concentrations reaching the systemic circulation. Systemic drug concentrations are then measured over 24 to 48 hours following the infusion.

Another double balloon catheter design may utilize only 2 supplemental lumina and one main lumen for blood transfer to the extracorporeal circuit. Each supplemental lumen can supply fluids to one of the balloons.

THE PUMP

The venous pressure provides the pressure for passage of blood to the extracorporeal circuit. The function of the pump is to continue the movement of blood though the extracorporeal circuit and return it to the patient. The blood is removed from the body by a combination of gravitational displacement and the venous blood pressure. The pump does not generate a negative pressure and pull blood from the body. The pump does not generate a negative pressure and pull blood from the body. The pressure of the return flow of the blood from the extracorporeal circuit to the systemic veneous system should be less than about 300 mm Hg.

A variety of suitable pumps are commercially available. They come in a number of designs. A preferred design is a centrifugal cardiopulmonary bypass pump that utilizes smooth surface rotators without relying on rotating vanes. These pumps have been used in long term support of cardiac bypass and in liver transplants. Such designs are shown in the following U.S. Pat. Nos.:
3,487,784, patented Jan. 6, 1970
Reissue 28,742, reissued Mar. 23, 1976
3,647,324, patented Mar. 7, 1972
3,864,055, patented Feb. 4, 1975
3,957,389, patented May 18, 1976
3,970,408, patented July 20, 1976
4,037,984, patented July 26, 1977

Such pumps are obtainable from Bio-Medicus, Inc., Minneapolis, Minn. 55344. This pump reacts to pressure changes automatically, and it has several inherent safety features. The centrifuge is volume dependent and the pump can decrease the flow rate if the venous drainage is interrupted. The pump can also slow itself down in instances of too much resistance to flow. For example, at a resistance of 700 mm Hg., the smooth rotator pump reduces its output flow to zero. In the event of power failure, the pump can automatically change over to battery power for uninterrupted pumping. This type of pump does not impose a negative pressure that pulls the blood flowing from the body and does not adversely affect the chemistry of the blood. They are herein characterized as smooth rotator pumps and referred to herein and in the claims as a "smooth rotator pump."

Another useful type of pump is the centrifugal pump such as the vane (impeller) design sold by Sarns Inc/3M, Ann Arbor, Mich. 48106. Another type of pump is the roller bearing pump. The preferred pump for practicing the process of the invention is the smooth rotator pump.

BLOOD DETOXIFICATION

The contaminated blood captured by the double balloon catheter is fed through tubing to the pump and then to a blood detoxification step. The process will be successful even if the anti-cancer agent is not completely removed from the blood. The important point is that the amount of anti-cancer agent in the body be kept below toxicity levels. One hundred percent removal of any drug is seldom possible and generally not practical. The decontamination of the blood may be effected by a number of standard procedures known to the art. These include the use of detoxification means, such as a hemoperfusion cartridge and/or hemodialysis and/or hemofiltration and/or hemoadsorbtion through antibodies or biological ligands or molecules able to render them nontoxic, to clear the blood of the antineoplastic agent and allow the re-administration of the patient's own detoxified blood. The detoxification step comprises any process by which the concentration of the anti-cancer agent in the blood can be removed so that the blood can be returned to the body without causing systemic toxicity.

Hemoperfusion involves the passage of the contaminated blood over a solid surface detoxicant particulate mass that separates the contaminant by sorption or by ion exchange. A variety of these detoxicant particulates are known in the art. A common one is carbon or graphite. Activated carbon is commonly employed for this purpose. A common concern with the use of such particulates is stated in Clark, U.S. Pat. No. 4,048,064, patented Sept. 13, 1977, at col. 1, lines 8-23, as follows: "While the technique is initially very effective, such previous attempts at hemoperfusion have been plagued by very high losses of white cells and platelets (cite) as well as clotting, sludging, and channeling of blood in the column. The column then becomes ineffective and the patient suffers thromobocytopenia. Further, fine detoxicant particles tend to be released into the blood stream to become emboli in blood vessels and organs such as the lungs, spleen, and kidneys (cite)."

Clark describes the use of a heparin loaded polymer coating of the carbon particles, preferably activated carbon, to provide a semipermeable coating on the particles. A mass of the coated particles is then placed in a nylon mesh sack and the sack is placed in a container that has an inlet on one end and an outlet on the other. The blood is then fed to the container and passed through the bed of coated activated carbon particles where it penetrates the polymer coating, obtains heparin treatment and the contamination is removed by adsorption.

Winchester, et al. *Clinical Toxicology*, 17 (4), pp. 557-569 (1980) describe the use of a variety of sorbents for the detoxification by hemoperfusion of contaminated blood where the contamination was a chemotheraputic agent (drug). The article shows that polymer coated and uncoated particulate detoxicants can be used to materially reduce the contamination of the blood. Like Clark, acrylic hydrogels were used to coat the particles. Nonionic exchange resins are also described in the article. The authors found that a certain pyrolized resin was an effective absorbant.

Clark and Winchester, et al. are incorporated herein by reference. Needless to say, modifications of the separation canisters suggested by Clark and Winchester, et al. will be dictated by the blood flow rate and the degree of drug contamination. If the blood flow rate is higher in the separation canister containing the bed or mass of the sorbents than the particle strength of the sorbent, then the techniques of treating the sorbents or operating the separation should be altered. For example, if the sorbent breaks up in the course of hemoperfusion, then the sorbent should be larger and the flow rates of the contaminated blood into and through the bed should be lower. Another approach to such a problem is to eliminate any leachables such as heparin from the polymer coating. This will make the coating more resistant to breakup. The problem may also be helped by the use of stronger coatings which means the use of, e.g., a slightly more crosslinked polymer than those conventionally employed in the art for this purpose.

Hemodialysis has been previously employed in cancer chemotherapy, see Galletti, Portocaval Hemofiltration During The Anhepatic Phase In Isolated Liver Perfusion, *Trans. Amer. Soc. Artif. Int. Organs*, vol. XII, pp. 20-24, 1966, and Winchester, et al., Dialysis and hemoperfusion of poisons and drugs, *Trans. Amer. Soc. Artif. Int. Organs*, vol. XXIII, pp. 762-842.

Hemofiltration is a well defined technology and is characterized in a number of texts. It involves the filtration from the contaminated blood of the antineoplastic agent through membrane walls. Details of the process and the apparatus used in effecting the process are described in inter alias Malchesky, *Membrane Plasma Separation: Critical Issues*, Therapeutic Apheresis: A Critical Look, edited by Y. Nose', P. S. Malchesky, and J. W. Smith, ISAO Press, No. 304, pp. 93-101, Cleveland, Ohio U.S.A., 1984; Vassilieff, et al., *Plasmapheresis Between a Rotating Truncated Cone and a Microporous Plate*, Therapeutic Apheresis: A Critical Look, edited by Y. Nose', P. S. Malchesky, and J. W. Smith, ISAO Press, No. 304, pp. 102-114, Cleveland, Ohio U.S.A., 1984; Raff, et al., *Influence of Geometric Parameters on Filtration Flux in Plasma Filters*, Therapeutic Apheresis: A Critical Look, edited by Y. Nose', P. S. Malchesky, and J. W. Smith, ISAO Press, No. 304, pp. 115-121, Cleveland, Ohio U.S.A., 1984; Koga, et al., *Investigation of the Clinical Properties of Various Filters for Double and Triple Filtration Plasmapheresis*, Therapeutic Apheresis: A Critical Look, edited by Y. Nose', P. S. Malchesky, and J. W. Smith, ISAO Press, No. 304, pp. 171-175, Cleveland, Ohio U.S.A., 1984; Tani, et al., *New Anticancer Treatment by Hemoperfusion with Endotoxin Immobilized Fiber*, Therapeutic Apheresis: A Critical Look, edited by Y. Nose', P. S. Malchesky, and J. W. Smith, ISAO Press No. 304, pp. 202-207, Cleveland, Ohio U.S.A., 1984; Fabbri, et al., *Twelve-Hour Hemoperfusion on Activated Coated Charcoal with Heparin and Prostacyclin in Healthy Rabbits*, Therapeutic Apheresis: A Critical Look, edited by Y. Nose', P. S. Malchesky, and J. W. Smith, ISAO Press, No. 304, pp. 208-216, Cleveland, Ohio U.S.A., 1984; and Gelfand, et al., *Extracorporeal Induction of In Vivo Suppressor Cell Predominance by Plasmaleukapherisis: An Alternative to Cyclosporin in Renal Transplantation*, Therapeutic Apheresis: A Critical Look, edited by Y. Nose', P. S. Malchesky, and J. W. Smith, ISAO Press, No. 304, pp. 217-240, Cleveland, Ohio U.S.A., 1984. A detailed review of the subject of hemofiltration can be found in Henne, et al., *Membrane Technology for Plasmapheresis*, Plasma Separation and Plasma Fractionation, pp. 164-179 (Karger, Basel 1983). The disclosure of these references as they relate to hemofiltration especially in extracorporeal circuits are incorporated herein by reference.

An excellent overview of hemofiltration and hemodialysis is presented in Horton, et al., *Continuous arteriovenous hemofiltration: An alternative to hemodialysis*, American Journal of Hospital Pharmacy, vol. 45, June 1988, pp. 1361-1368. The use of hemodialysis and hemoperfusion to remove antineoplastic agents is described in Kamidono, et al., *A Fundemental Study Of*

*Regional Chemotherapy Given By Intraarterial Infusion With Concomitant Hemodialysis And Hemoperfusion*, Investigative Urology, vol. 19, No. 3, pp. 176–178, 1981;

Hemofiltration and hemodialysis can be carried out with a renal® Hemofiltration System, sold by renal systems, a division of Minntech Corporation, Minneapolis, Minn. 55441.

The chemical, physical or immunologic means for precipitation of the chemotherapeutic agent or the immunomodulating biologicals include separation through hemoadsorbtion using antibodies or biological ligands or molecules able to render them nontoxic, and/or to clear the blood of the antineoplastic agent and allow the re-administration of the patient's own detoxified blood. These systems have enjoyed extensive consideration in the art and descriptions of them may be found in the following publications: Pineda, *Method For Selective Removal Of Plasma Constituents*, Therapeutic Apheresis and Plasma Perfusion, pp. 361–373, 1982, Alan R. Liss, Inc., 150 Fifth Avenue, New York, N.Y. 10011; Saal, et al., *Extracorporeal Modification Of Plasma And Whole Blood*, Therapeutic Apheresis and Plasma Perfusion, pp. 375–384, 1982, Alan R. Liss, Inc., 150 Fifth Avenue, New York, N.Y. 10011; and Messerschmidt, et al., *The Use Of Protein-A In The Treatment Of Malignancy: Rationale And The NCI Experience*, Therapeutic Apheresis and Plasma Perfusion, pp. 385–390, 1982, Alan R. Liss, Inc., 150 Fifth Avenue, New York, N.Y. 10011. The disclosure of these references as they relate to the chemical, physical or immunologic means for precipitation of the chemotherapeutic agent or the immunomodulating biologicals are incorporated herein by reference.

The pressure of the blood after detoxification in the extracorporeal circuit is measured in the tubing. The pressure in the tubing must be maintained above systemic venous pressure. The detoxified blood is returned to the body through the subclavian veins via a catheter percutaneously placed. Alternatively, the blood may be returned through a return lumen that traverses the double balloon catheter and delivers the detoxified blood to the right atrium or the superior vena cava.

CHEMOTHERAPY OF THE ORGAN

The prior art illustrates a variety of procedures for supplying a chemotherapuetic agent to an organ containing a malignant tumor. These procedures may be used in the practice of the process of this invention. For example, using the Seldinger technique, a perfusion catheter can be introduced into the femoral artery. With fluoroscopy and standard arteriographic techniques, the catheter can be manipulated into the hepatic artery or, if the tumor is localized, into the branch of the hepatic artery that supplies the tumor. Arterial blood reaches normal liver cells from two sources, the hepatic artery and the portal vein. In the normal individual, 75% of the volume of the arterial blood that perfuses normal liver cells is delivered by the portal vein, while the hepatic artery supplies only about 25%. The catheter can be sutured to the skin of the groin to maintain its position. This catheter can be used for infusion of suitable anti-cancer agents directly into the artery that supplies the tumor. This procedure can be repeated as often as it would be clinically useful.

Illustrative of suitable chemotherapuetic agents for use in the practice of this invention are Adriamycin (doxorubicin), fluorinated pyrmidines (5-FU or floxuridine (FUDR), cisplatin, Mitomycin C, cyclophospamide, methotrexate, vincristine, Bleomycin, FAMT, and any other anti-cancer agent. As pointed out above, the invention may be employed to effect treatment of organs with biologicals (immunomodulators) as part of a cancer therapy. Illustrative immunomodulating biologicals suitable for use in the invention are alpha interferon, beta interferon, gamma interferon, interleukin-2, interleukin-3, tumor necrosis factor, granulocyte-macrophage colonystimulating factors, and the like.

Selective arteriography can be performed through the arterial infusion catheter prior to drug infusion and again prior to removal of the catheter to demonstrate the anatomic distribution of the supplying arteries and to evaluate any early changes in the vascular pattern of the tumor or the liver. In patients with accessory blood supply to the liver from either the superior mesenteric artery or the left gastric artery or both, the vessel which supplies the main bulk of the tumor is the vessel that is infused. If more than one artery supplies large volumes of blood to the tumor, two infusion catheters may be used, one placed through each femoral artery, and dividing the infused dose of drug between the two catheters.

The arterial catheter can be removed immediately following postinfusion arteriography, and the vena cava catheter can be removed after the last hepatic venous blood samples have been collected. Heparin can be given intravenously at least 15 minutes before the extracorporeal circuit is opened and discontinued or reversed with protamine shortly after deflation of the balloons but before removal of the venous catheter.

Liver function tests will be measured before therapy, daily for three days following therapy, and then at least monthly for at least 3 months to evaluate the possibility of functional alterations of the liver, either as a result of the perfusion technique, drug toxicity or growth of the tumor.

The process of the invention can be used repeatedly over periods of months or years and as frequently as desired, since the catheter should not produce permanent alteration of anatomy at the puncture site, at the site of arterial infusion, or at the site where the balloons are inflated.

With respect to FIG. 1, there is shown the featured components of the apparatus assembly of the invention used to practice the process of the invention in relation to a human body 2. Liver 3 is supplied with cancer therapy drugs from syringe 4 through tubing leading to catheter 6 located in hepatic artery 5. The hepatic venous blood containing anti-cancer concentrations of chemotherapuetic agent is passed via the hepatic veins 7 to the double balloon catheter located in IVC 1. The balloons of the double balloon catheter are positioned central and peripheral of the hepatic veins 7. The contaminated blood is passed through the double balloon catheter to tubing 17 to a point exterior to the body 2, thence to a pump 21 such as a Bio Medicus BP-50 Bio-Pump having a priming volume of 48 ml, containing two rotator cones and providing a maximum flow rate of 5 liters per minute. Pump 21 moves the blood through the extracorporeal circuit at relatively constant low pressure, the object being to avoid raising or lowering the fluid pressure of the total circuit ranging from the hepatic veins through the return to the body. The contaminated blood is transported through tubing 41 into detoxification zone 43, which in this case is a hemoperfusion cartridge containing activated carbon. Suitable cartridge systems are obtainable from Clark Research and Development, Inc., New Orleans, La. 70121 and from Gambro Dialysatoren KG, d-7450 Hechingen, Federal Republic of Germany AUT 224 (sold under the trademark of ADSORBA ®). The detoxified blood is passed through tube 44 to effect infusion through the subclavian vein (not shown) by standard procedures in the art.

With respect to FIG. 2, there is shown the relationship of inferior vena cava 1 to liver 3, hepatic veins 7 and portal veins 5. The hepatic artery is not shown in the drawing. Double balloon catheter 9 comprises central balloon 11 and peripheral balloon 12, each in juxtaposition to cylindrical fenestration zone 8. Zone 8 contains fenestrations 13 sufficient in total area to allow the complete removal of the hepatic venous flow into the catheter 9. The hollow interior (main lumen) of catheter 9 is of sufficient size to completely remove the blood from the hepatic veins without elevating hepatic back pressure. Catheter 9 is provided with channel 15 that is used to inject fluid into the balloons 11 and 12 for inflation or to withdraw fluids for deflation. The venous flow is passed through catheter 9 into openly connected tube 17. Tube 17 may be interrupted by a pressure monitor the same as assembly A, discussed below, that is later provided in the extracorporeal circuit. Tube 17 may connect directly with pump 21 or to Y-fitting 19, as shown. Also connected to Y-fitting 19 is ancillary feed system B comprising tube 23, Y-fitting 25, and multiple IV spikes 29 and 33 each connected to tubes 30 and 31 respectively, and each is provided with a clamp, 27 and 28, respectively. These line can be used for the introduction of medications as required.

Pump 21 is a smooth rotator pump design and a particularly desirable pump is a Bio Medicus BP-50 Bio-Pump having a priming volume of 48 ml, containing two rotator cones and providing a maximum flow rate of 5 liters per minute. The contaminated blood is gently pushed between the smooth rotators 37 in zones 35 and issued from the pump through port 39 into tube 41. Tube 41 is connected to cartridge or canister 43 containing a meshed sack of activated carbon particles coated with an acrylic resin containing heparin, see Clark, supra. The outflow from cartridge 43 is fed to tube 45 and then to tube 47 that is connected to pressure monitoring assembly A. Pressure monitoring assembly A comprises a pressure monitor gauge 55 connected to fluid membrane vessel 53 that contains a thin membrane that separates the gauge 55 from the blood in vessel 53 and responds to the fluid pressure of the blood in vessel 53. That response is read by the gauge. Vessel 53 is connected to tubing 57, that is connected to stopcock 52. Stopcock 52 is connected to flexible tubing 59 that in turn is connected to stopcock 51, the latter secured in fitting 49.

Blood from tubing 47 is passed to Y-connector 63 via tubing 61, then to tubings 65 and 67. Tubings 65 and 67 are each connected to catheter 69 and another catheter (connected to tube 65) not shown. These catheters are provided for returning the purified blood to the subclavian veins.

In FIG. 3, there is shown a double balloon catheter design that can have up to a 24 French (Fr) O.D. Zone 100 is provided with slotted fenestrations 104 in the solid plastic tubing 102. The open end 118 terminates the catheter. End 118 is tapered to the caliber of an angiographic guide wire that will, under fluoroscope control, allow the catheter to be advanced from the femoral vein to the proper location in the inferior vena cava without risk of injury to the interior of the vessels. Appropriate guide wires may be, for example, 0.035, 0.038, or 0.045 inch in diameter. During treatment, the catheter end hole is closed using a standard angiographic apparatus (tipoccluding wire), that consists of a thin wire long enough to traverse the length of the catheter at the end of which is a stainless steel bead just large enough to obstruct the catheter's end-hole when advanced into it (similar to a metal stopper that closes the outlet from a sink when advanced).

Alternatively, the end hole can be made 7-12 Fr in diameter in order to accommodate a return catheter. The return catheter can be used to return treated blood to the systemic circulation. The return catheter is advanced over a guide wire through the main lumen of the double balloon catheter and through the end hole 118 into the right atrium or superior vena cava. The return catheter can be made to gradually taper its O.D. by decreasing its wall thickness, leaving the I.D. constant, since the location of the tip of the return catheter is not critical. The length over which the catheter tapers is arbitrary. The taper is constructed so that the tip of the catheter is its narrowest O.D. and the O.D. increases toward the femoral vein. As this return catheter is advanced through the lumen of the main catheter the tip easily passes through the end hole 118 of the double balloon catheter. The tapered end of the return catheter is advanced until it obstructs the end hole 118, preventing systemic blood from entering the double balloon catheter when the balloons are inflated but leaving an open lumen through the return catheter to return blood beyond the isolated venous segment without mixing with contaminated blood.

The catheter tubing (body) can be made of a variety of plastic materials such as polypropylene, polyethylene, polyvinylchloride, ethylene vinylacetate copolymers, polytetrafluoroethylene, polyurethane, and the like. A favorable plastic combination for catheters containing a return lumen are a homogeneous mixture of high density polyethylene and linear low density polyethylene. That combination gives favorable stiffness at ambient conditions and allows the use of especially thin wall thicknesses. When the surface of the catheter is made of a plastic that is difficult to bond with a balloon, the plastic may be treated first by one or more of a number of well known methods that make bonding possible. The methods include plasma treatment, ozone treatment, and the like. Balloons 110 and 114 may be made from a plurality of elastomeric materials such as latex rubber, polyurethanes, spandex type polyurethanes, EPDM rubber, and the like. The balloons are typically adhesively bonded at sheath surfaces 108 and 112, respectively. A wide variety of adhesives may be employed. Polyacrylonitrile type adhesives, rubber latex adhesives and the like may be used to secure the balloon to the sheath surfaces 108 and 112.

With respect to FIG. 4, there is shown a cross section of a typical catheter design such as that shown in FIG. 3. The interior of the catheter contains main lumen 120 and 4 additional lumina 124 molded into the outer wall 122. The additional lumina can be used for the various functions described above.

With respect to FIG. 5, there is shown a cross section of another catheter design such as that shown in FIG. 3 but containing only three lumina. The interior of the catheter contains main lumen 130 and two supplementary lumina 131 molded into segment 133 of wall 135.

The supplementary lumina can be used for the various functions described above.

Figure 6:
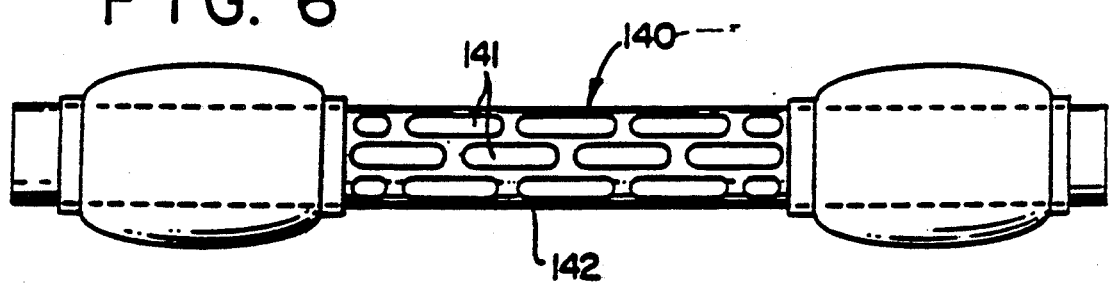
FIG. 6 shows a partial cross-sectional side view of another design of double balloon catheter useful in the process of the invention.
Figure 7:
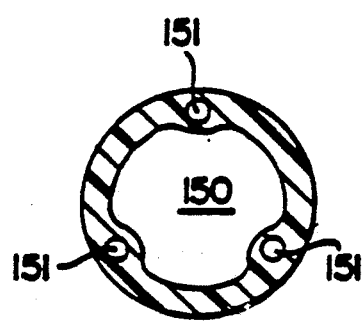
FIG. 7 shows a cross-sectional end view of the shaft of the double balloon catheter of FIG. 6.

With respect to FIG. 6, there is shown a double balloon catheter design which can have an outside diameter of 24 French such as in the fenestration zone 140 and an inside diameter of less than 22 Fr. Zone 140 is provided with slotted fenestrations 141 in the plastic tubing 142. With respect to FIG. 7, it is a cross sectional view of another typical catheter design showing a main lumen 150 and 3 supplemental lumina 151. FIG. 8 provides a more detailed schematic cross sectional side view of a typical double balloon catheter 161. In this depiction, the catheter sidewall 163 is penetrated by a plurality of fenestrations 165. The main lumen 169 contains at its periphery supplemental lumina 170, 171 and 173. Supplemental lumen 170 can be used to accommodate a guidewire, supplemental lumen 171 can be used to accommodate a pressure monitor, and supplemental lumen 173 is used to supply fluid to the balloons 166 and 167 through openings 175 and 177.

Though this invention has been described with emphasis on the treatment of cancer, it is quite apparent that the invention has broader application. The invention is useful for the treatment of any organ in which the treating agent would cause toxological effects if it entered the body's general circulation. For example, the invention could be applied to the treatment of infectious deseases of organs such as fungal deseases. A specific illustration would be the treatment of hepatic fungal infections with Amphotericen B. The procedures described above would be directly applicable to extracorporeal recovery of this agent and its isolation from entering the general circulation of the body during treatment of the liver with significant concentrations of this drug.

Therefore, the breadth of the invention encompasses the perfusing of a high concentration of an agent to treat an organ, such as anti-cancer agents through a body organ containing a tumor, without their entering the body's general circulation, removing them from the organ with effluent blood and transporting the contaminated blood to an extracorporeal circuit where the blood is treated to remove the contamination, and returning the treated blood to the body. The process prevents toxic levels of the agents from entering the body's general circulation while delivering lethal doses of the agents to the tumor.

I claim:

1. In a process for perfusing a high concentration of an agent through a body organ requiring treatment without contaminating the body's general circulation, the improvement comprising:

percutaneously inserting a single catheter having spaced balloons into the inferior vena cava of a body in which an organ is to be treated by perfusing a high concentration of a treating agent, said catheter being moved to a position in which inflation of the spaced balloons isolate effluent blood from the organ from the body's general circulation, said catheter having a lumen for removing blood derived from said organ;

inflating the balloons to isolate said effluent blood;

removing from the body through said lumen in said catheter essentially all of the effluent blood from said organ, said effluent blood containing said agent;

treating removed effluent blood to reduce the quantity of treating agent; and returning the thus treated blood to the body via the superior vena cava, a subclavian vein, a jugular vein or the right atrium.

2. The process of claim 1 wherein the organ is the liver.

3. The process of claim 2 wherein the treating agent is a cancer treating agent.

4. The process of claim 1 wherein said catheter includes a plurality of holes which place blood in the inferior vena cava in fluid flow communication with said lumen.

5. The process of claim 1 wherein said catheter includes a separate lumen for a guidewire and said catheter is inserted by use of a guidewire in said separate lumen.

* * * * *